US010386381B2

(12) United States Patent
Lair

(10) Patent No.: US 10,386,381 B2
(45) Date of Patent: Aug. 20, 2019

(54) DEVICE FOR RELEASABLY HOLDING AN ELONGATED OBJECT IN A PREDETERMINED ORIENTATION AND SYSTEM FOR TRANSPORTING AN ELONGATED OBJECT DISPOSED IN A PREDETERMINED ORIENTATION

(71) Applicant: GEN-PROBE INCORPORATED, San Diego, CA (US)

(72) Inventor: Gary D. Lair, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 190 days.

(21) Appl. No.: 15/431,053

(22) Filed: Feb. 13, 2017

(65) Prior Publication Data

US 2017/0153262 A1    Jun. 1, 2017

Related U.S. Application Data

(63) Continuation of application No. PCT/US2015/044870, filed on Aug. 12, 2015.
(Continued)

(51) Int. Cl.
*B01L 9/06* (2006.01)
*G01N 35/04* (2006.01)

(52) U.S. Cl.
CPC ............. *G01N 35/04* (2013.01); *B01L 9/06* (2013.01); *B01L 2200/025* (2013.01);
(Continued)

(58) Field of Classification Search
CPC ....................................................... B01L 9/06
See application file for complete search history.

(56) References Cited

U.S. PATENT DOCUMENTS 4,305,597 A    12/1981  McCarty
7,122,158 B2 *  10/2006  Itoh ........................... B01L 9/06
                                                        422/562
(Continued)

FOREIGN PATENT DOCUMENTS

JP    2005262041 A    9/2005

OTHER PUBLICATIONS

International Search Report issued in International Patent Application No. PCT/US2015-044870, 4 pages (dated Nov. 9, 2015).
(Continued)

*Primary Examiner* — Paul S Hyun
(74) *Attorney, Agent, or Firm* — Rothwell, Figg, Ernst & Manbeck, P.C.; Charles B. Cappellari

(57) ABSTRACT

A device for releasably holding an elongated object, such as a test tube, in a predetermined orientation includes a gripping element configured for circumferential expansion and contraction with respect to the object. An actuator element coupled to the gripping element is configured to effect circumferential expansion of the gripping element to an expanded configuration able to receive an end of the elongated object. A locking mechanism coupled to the actuator element is configured to lock the actuator element in a position holding the gripping element in the expanded configuration. A lock release mechanism is configured to be triggered by an elongated object inserted into the expanded gripping element and to release the locking mechanism, thereby allowing the biased gripping element to return to a contracted configuration gripping a portion of the object. The device and an object held thereby can be conveyed on a conveyor.

25 Claims, 5 Drawing Sheets

Related U.S. Application Data

(60) Provisional application No. 62/037,309, filed on Aug. 14, 2014.

(52) U.S. Cl.
CPC . *B01L 2300/021* (2013.01); *B01L 2300/0832* (2013.01); *G01N 2035/0406* (2013.01); *G01N 2035/0489* (2013.01)

(56) References Cited

U.S. PATENT DOCUMENTS

| | | | |
|---|---|---|---|
| 8,367,024 B2* | 2/2013 | Itoh | B01L 9/06 206/443 |
| 9,114,394 B2* | 8/2015 | Yanez | B01L 9/06 |
| 2005/0037502 A1 | 2/2005 | Miller | |
| 2005/0207945 A1 | 9/2005 | Itoh | |
| 2006/0222573 A1* | 10/2006 | Itoh | B01L 9/06 422/400 |
| 2008/0029672 A1 | 2/2008 | Ogura | |
| 2009/0308174 A1 | 12/2009 | Cutshall | |
| 2010/0015007 A1 | 1/2010 | Pedrazzini | |

OTHER PUBLICATIONS

Written Opinion issued in International Patent Application No. PCT/US2015-044870, 7 pages (dated Nov. 9, 2015).

International Preliminary Report on Patentability issued in International Patent Application No. PCT/US2015/044870, 9 pages (dated Feb. 14, 2017).

JPO, Official Action, Japanese Patent Application No. 2017-508067, dated Feb. 2, 2018.

Notice of Reasons for Rejection dated Jan. 31, 2019 issued in Japanese Patent Application No. 2017-508067. (9 pages).

* cited by examiner

DEVICE FOR RELEASABLY HOLDING AN ELONGATED OBJECT IN A PREDETERMINED ORIENTATION AND SYSTEM FOR TRANSPORTING AN ELONGATED OBJECT DISPOSED IN A PREDETERMINED ORIENTATION

PRIORITY CLAIM/CROSS REFERENCE TO RELATED APPLICATION

This application is a continuation under 35 U.S.C. 120 of International Application No. PCT/US2015/044870, filed Aug. 12, 2015 and designating the United States, which claims the benefit under 35 U.S.C. 119(e) of U.S. Provisional Application No. 62/037,309, filed Aug. 14, 2014, the respective disclosures of which are hereby incorporated by reference.

FIELD OF THE DISCLOSURE

This disclosure relates to a device for releasably holding an elongated object, such as a tubular container (e.g., test tube), in a predetermined orientation with respect to the device, such as in an upright orientation. The device can be set to an open position and is configured to automatically close onto the object in a holding position when the object is inserted into the device. The device may be configured to cooperate with a conveyor mechanism, such as a conveyor belt or track, so that the object is held in a preferred orientation while being conveyed on the conveyor mechanism. The disclosure also relates to a system for transporting an elongated object disposed in a predetermined orientation, including a device for releasably holding the objection in a predetermined position with respect to the device and a conveyor for conveying the device and the object held thereby.

BACKGROUND

Conveying a relatively narrow article that is inherently unstable or impossible to maintain in an upright position imposes certain challenges for securely transporting such an article. For example, in a hospital or clinical laboratory, it may be desirable to transport a sample or reagent containing receptacle, such as a test tube, from one location to another (e.g., from a first processing instrument to a second processing instrument) in an upright orientation, so that the contents of the receptacle are retained during transport and can be accessed by an automated pipettor at a subsequent location. The instability of the test tube makes it impossible to transport in an upright orientation on a conveyor mechanism without some form of support.

Conveyors suitable for use in a laboratory or in other applications in which articles are moved along a sequential process may comprise commercially-available, so-called puck conveyors, or puck handling systems, configured to convey or otherwise manipulate circular, disc-like devices, having a configuration reminiscent of an ice hockey puck, and which can be configured to hold an article that is to be conveyed, along with the "puck," by the conveyor. Such conveyor systems include the model X45 conveyor platform and the model X45e drive and puck handling units, operable with the XUPP 43 interface puck, available from FlexLink AB, Göteborg, Sweden. Holding a narrow article, such as a test tube or other narrow container, on such a puck device allows such commercially-available, readily scalable and configurable conveyors to be used to transport the containers.

SUMMARY

Aspects of the disclosure relate to a device for releasably securing an elongated object in a predetermined orientation with respect to the device. The device comprises a gripping element configured for circumferential expansion and contraction, an actuator element coupled to the gripping element and configured to effect circumferential expansion of the gripping element, upon operation of the actuator element, to an expanded configuration able to receive an end of the elongated object, a locking mechanism coupled to the actuator element and configured to lock the actuator element in a position holding the gripping element in the expanded configuration, and a lock release mechanism configured to be triggered by an elongated object inserted into the device to release the locking mechanism. The gripping element is circumferentially biased so as to cause the gripping element to circumferentially contract around the received end of the elongated object upon release of the locking mechanism.

According to further aspects of the disclosure, the device further comprises a base, and the actuator element comprises an actuator ring rotatably mounted within a portion of the base such that partial rotation of the actuator ring with respect to the base in a first direction causes circumferential expansion of the gripping element and circumferential contraction of the gripping element causes partial rotation of the actuator ring with respect to the base in a second direction opposite the first direction.

According to further aspects of the disclosure, the gripping element comprises a torsion spring having coils defining a circumference of the gripping element, a first end fixed to the base, and a second end fixed to the actuator ring. The coils are configured to circumferentially expand against a bias of the torsion spring when the actuator ring is rotated in the first direction with respect to the base to move the second end angularly in the first direction with respect to the first end, and the coils are configured to contract when the bias of the torsion spring moves the second end and the actuator ring angularly in the second direction with respect to the first end and the base.

According to further aspects of the disclosure, the torsion spring is at least partially disposed with an opening formed at the center of the actuator ring.

According to further aspects of the disclosure, the locking mechanism comprises a spring plate with at least two lock pins protruding therefrom, a spring constructed and arranged to bias the spring plate toward the actuator element, and pin recesses formed in a side of the actuator element facing the spring plate, and corresponding in number with the number of lock pins protruding from the spring plate. The lock pins are moved into alignment with the pin recesses when operation of the actuator element causes circumferential expansion of the gripping element to the expanded configuration so that the spring thereby moves the spring plate toward the actuator element and pushes the lock pins into the pin recesses to rotationally lock the actuator element with respect to the spring plate.

According to further aspects of the disclosure, the release mechanism comprises a release pin protruding from the spring plate and constructed and arranged to be contacted by an elongated object inserted into the device and so as to push the spring plate against the bias of the spring away from the actuator element until the lock pins of the spring plate are withdrawn from the pin recesses of the actuator element.

According to further aspects of the disclosure, the device further comprises a circular base having an upper portion and a lower portion. The lower portion includes an upper radial flange and a lower radial flange and a core disposed between the upper and lower radial flanges. The core has a smaller diameter than either of the upper and lower radial flanges.

According to further aspects of the disclosure, the base is configured to cooperate with a conveyor mechanism to transport the device and a container held thereby along the conveyor mechanism.

According to further aspects of the disclosure, the base is circular, and the device further includes an outer ring disposed on the base so as to be rotatable with respect to the base about a central axis of the circular base.

According to further aspects of the disclosure, the outer ring is made from a magnetic or magnetically-responsive material.

According to further aspects of the disclosure, the device further comprises an automatic identification element encoded with an identifying code so that the device or an object carried thereby can be automatically identified in an automated process or instrument in which the device is employed.

According to further aspects of the disclosure, the automatic identification element comprises an RFID tag.

Further aspects of the disclosure are embodied in a system for transporting an elongated object disposed in predetermined orientation. The system comprises a holding device for releasably securing an elongated object in a predetermined orientation with respect to the device and a conveyor platform configured to support and convey the holding device. The holding device comprises a gripping element configured for circumferential expansion and contraction, an actuator element coupled to the gripping element and configured to effect circumferential expansion of the gripping element, upon operation of the actuator element, to an expanded configuration able to receive an end of the elongated object, a locking mechanism coupled to the actuator element and configured to lock the actuator element in a position holding the gripping element in the expanded configuration, and a lock release mechanism configured to be triggered by an elongated object inserted into the device to release the locking mechanism. The gripping element is circumferentially biased so as to cause the gripping element to circumferentially contract around the received end of the elongated object upon release of the locking mechanism.

According to further aspects of the disclosure, the holding device comprises a base having a lower collar extending laterally therefrom, and the conveyor platform comprises a track having a side wall with a retainer flange extending laterally therefrom, wherein the retainer flange extends over the lower collar when the holding device is supported on the conveyor platform.

According to further aspects of the disclosure, the base of the holding device has an upper collar extending laterally therefrom at a spaced apart position above the lower collar, and the retainer flange extends laterally between the lower collar and the upper collar when the holding device is supported on the conveyor platform.

According to further aspects of the disclosure, the conveyor platform includes a movable belt on which the holding device is supported and which is configured to convey the holding device.

According to further aspects of the disclosure, the actuator element of the holding device comprises an actuator ring rotatably mounted within a portion of the base such that partial rotation of the actuator ring with respect to the base in a first direction causes circumferential expansion of the gripping element, and circumferential contraction of the gripping element causes partial rotation of the actuator ring with respect to the base in a second direction opposite the first direction.

According to further aspects of the disclosure, the gripping element of the holding device comprises a torsion spring having coils defining a circumference of the gripping element, a first end fixed to the base, and a second end fixed to the actuator ring. The coils are configured to circumferentially expand against a bias of the torsion spring when the actuator ring is rotated in the first direction with respect to the base to move the second end angularly in the first direction with respect to the first end. The coils are configured to contract when the bias of the torsion spring moves the second end and the actuator ring angularly in the second direction with respect to the first end and the base.

According to further aspects of the disclosure, the torsion spring is at least partially disposed with an opening formed at the center of the actuator ring.

According to further aspects of the disclosure, the locking mechanism of the holding device comprises a spring plate with at least two lock pins protruding therefrom, a spring constructed and arranged to bias the spring plate toward the actuator element, and pin recesses formed in a side of the actuator element facing the spring plate, and corresponding in number with the number of lock pins protruding from the spring plate. The lock pins are moved into alignment with the pin recesses when operation of the actuator element causes circumferential expansion of the gripping element to the expanded configuration so that the spring thereby moves the spring plate toward the actuator element and pushes the lock pins into the pin recesses to rotationally lock the actuator element with respect to the spring plate.

According to further aspects of the disclosure, the release mechanism of the holding device comprises a release pin protruding from the spring plate and constructed and arranged to be contacted by an elongated object inserted into the device and so as to push the spring plate against the bias of the spring away from the actuator element until the lock pins of the spring plate are withdrawn from the pin recesses of the actuator element.

According to further aspects of the disclosure, the base of the holding device is circular and the device further includes an outer ring disposed on the base so as to be rotatable with respect to the base about a central axis of the circular base.

According to further aspects of the disclosure, the outer ring is made from a magnetic or magnetically-responsive material.

According to further aspects of the disclosure, the holding device further comprises an automatic identification element encoded with an identifying code so that the holding device or an object carried thereby can be automatically identified in an automated process or instrument in which the device is employed.

According to further aspects of the disclosure, the automatic identification element of the holding device comprises an RFID tag.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

DETAILED DESCRIPTION

Figure 1:
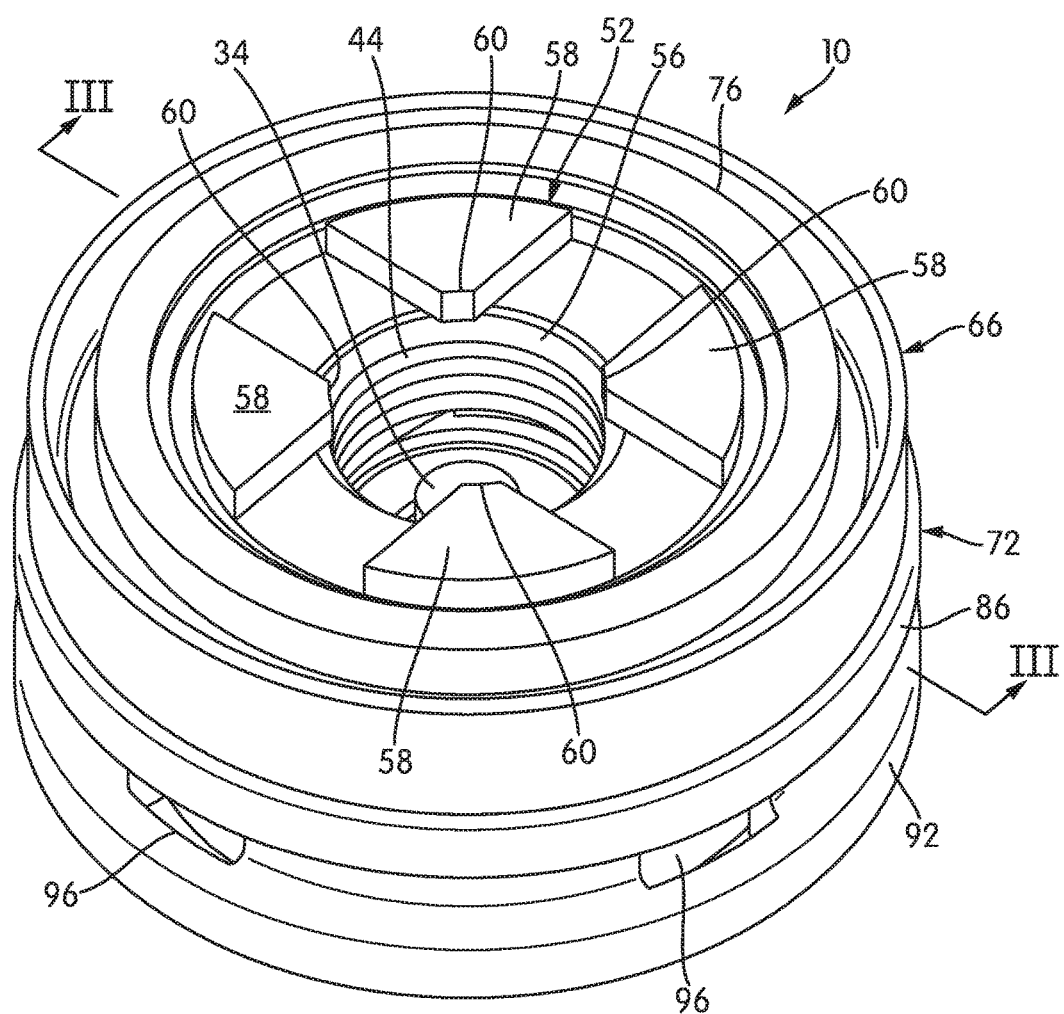
FIG. 1 is a top perspective view of a device for releasably holding a receptacle in an upright position.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, device, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, device, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

Figure 2:
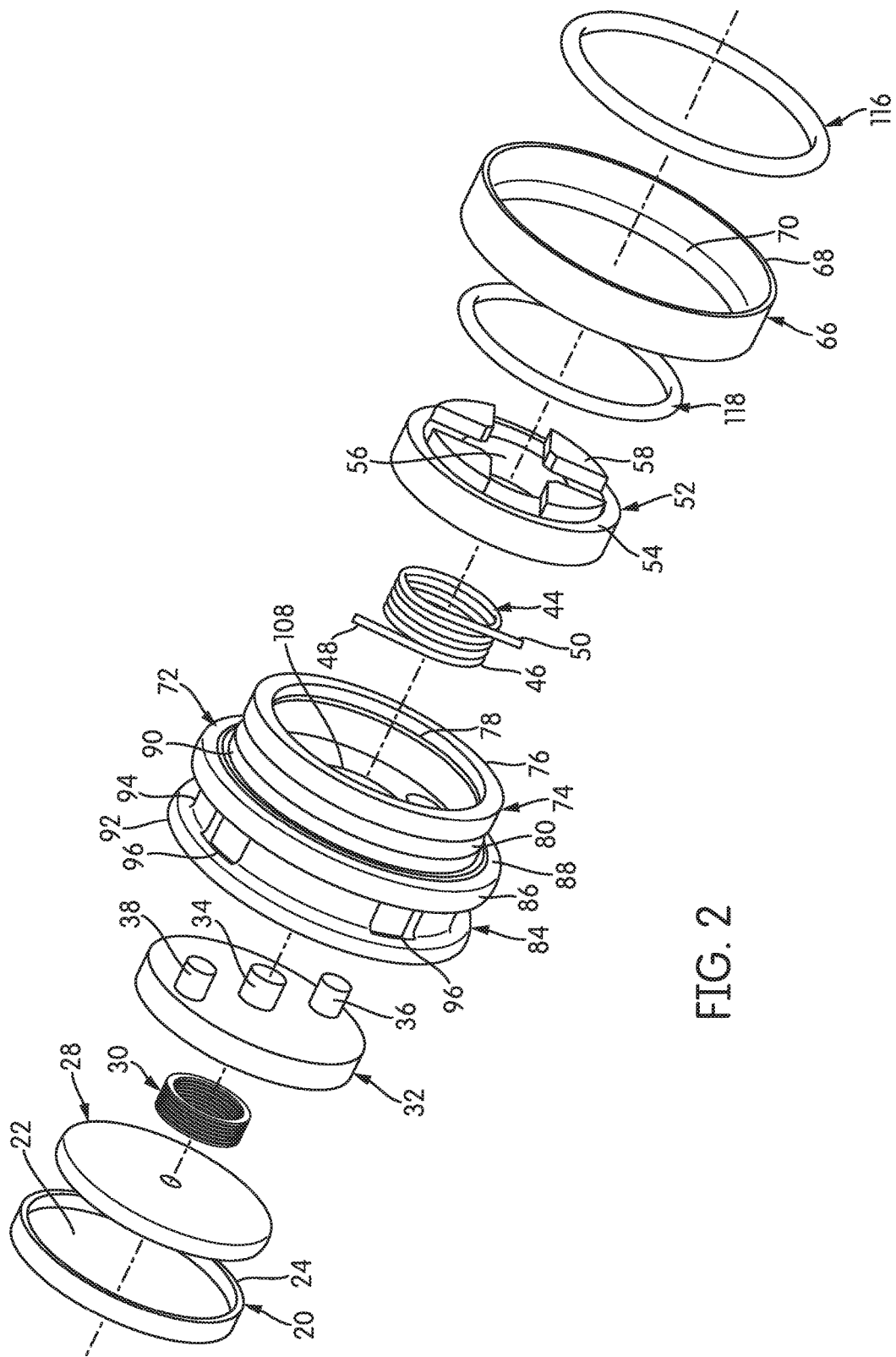
FIG. 2 is an exploded perspective view of the device.
Figure 3:
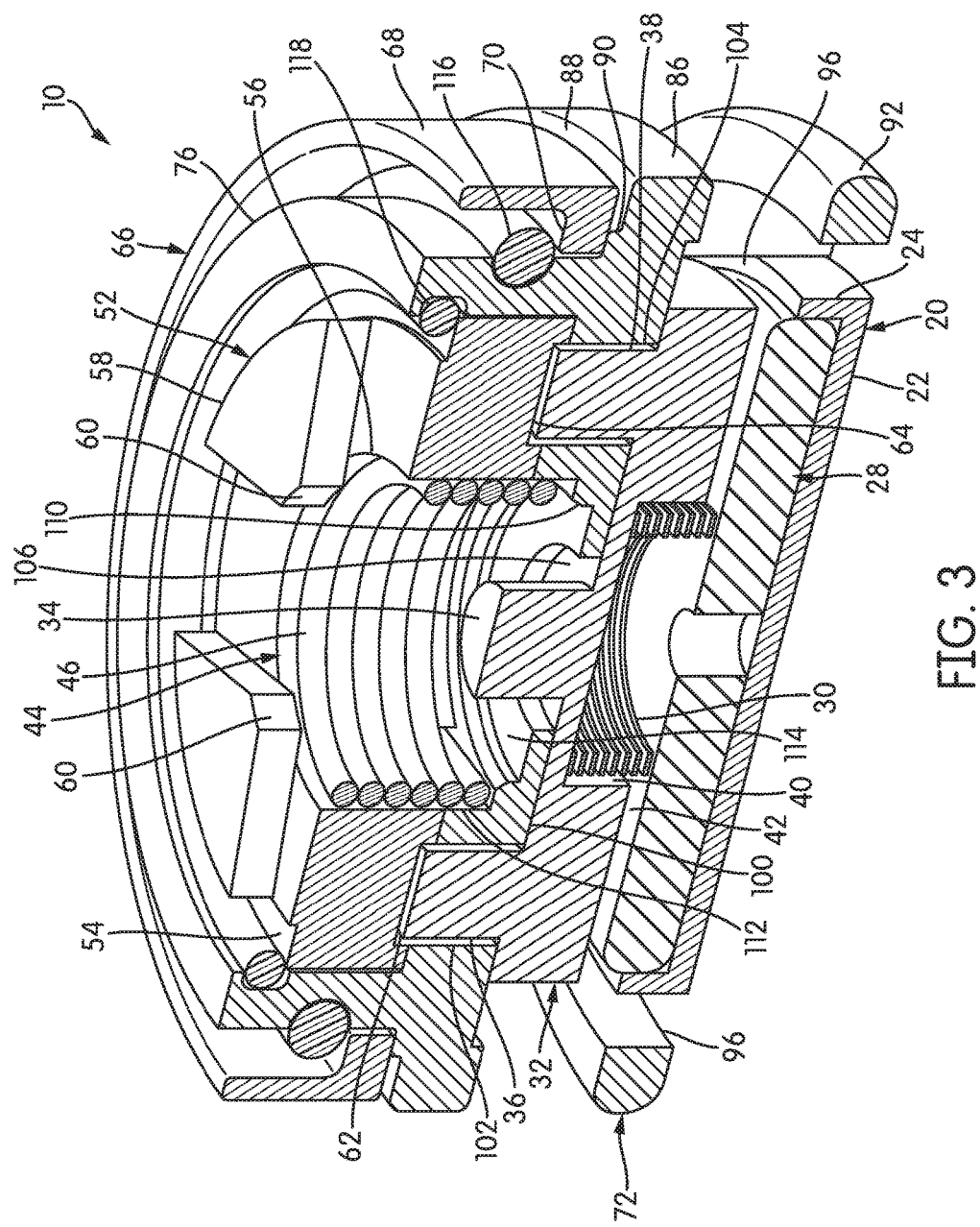
FIG. 3 is a cross-sectional, perspective view along the line III-III in FIG. 1.

An exemplary embodiment of a device 10 for holding a receptacle or other elongated object in a predetermined position with respect to the device 10 is shown in FIGS. 1-3. In general, the device 10 is configured to releasably secure an elongated object, such as a tubular (e.g., cylindrical) container in a predetermined orientation with respect to the device, such as in an upright orientation. In an exemplary embodiment, as illustrated in the drawings, the device 10 comprises a base 72 that includes an upper portion 74 and a lower portion 84 with a transversely-extending midwall 100 generally disposed at the interface of the upper portion 74 and lower portion 84. The base 72 is generally hollow at the upper portion 74 and the lower portion 84 with only the midwall 100 extending through an inner portion of the base 72.

The device 10 includes a gripping element that is configured for circumferential expansion and contraction with respect to the elongated object. In one embodiment, the gripping element includes a torsion spring 44 having coils 46 that surround a portion of the elongated object and selectively expand or contract with respect to the elongated object and which includes a lower end (tail) 48 and an upper end (tail) 50. In the illustrated embodiment, the torsion spring 44 has a circular cross-section but any cross-sectional shape may be used.

The device 10 further includes an actuator element coupled to the gripping element (e.g., torsion spring 44) and configured to effect circumferential expansion of the gripping element, upon operation of the actuator element, to an expanded configuration able to receive an end of the elongated object. In an embodiment, the actuator element includes an actuator ring 52 that is disposed within the upper portion 74 of the base 72. In various embodiments, both the base 72 and the actuator ring 52 are circular, and the actuator ring 52 is coaxially arranged with respect to the base 72 and is configured to be rotatable about its central axis relative to the base 72. In an exemplary embodiment, the torsion spring 44 is disposed within a central hole 56 of the actuator ring 52. The lower tail 48 of the torsion spring 44 is fixed to a portion of the base 72, and the upper tail 50 of the torsion spring 44 is fixed to a portion of the actuator ring 52. A spring plate 32 is disposed within the lower portion 84 of the base 72 and is retained therein by a retainer plate 20 that, in the illustrated embodiment, is press-fit into the lower portion 84. In various embodiments, both the base 72 and the spring plate 32 are circular, and the spring plate 32 is coaxially arranged with respect to the base 72. An axial spring 30 is disposed between the retainer plate 20 and the spring plate 32 and biases the spring plate 32 away from the retainer plate 20 and toward the midwall 100 of the base 72.

Further exemplary details regarding the individual components of the device 10, their interrelation, and the assembly of the device 10, as well as the operation and function of the device and each of the components, will now be described.

The upper portion 74 of the base 72 includes a peripheral wall 76 extending axially from the midwall 100. In the illustrated embodiment, in which the base 72 is circular, the peripheral wall 76 is cylindrical. An inner retaining ring groove 78 is formed on an inner surface of the peripheral wall 76, and an outer retaining ring groove 80 is formed on an outer surface of the peripheral wall 76.

The lower portion 84 of the base 72 comprises an upper collar, or radial flange, 86. In the illustrated embodiment, the upper collar 86 is generally coextensive of the midwall 100. Upper collar 86 defines an annular shoulder 88 extending about the base 72. Upper collar 86 further includes a raised surface 90 at the inner periphery of the shoulder adjacent the junction between the upper collar 86 and the cylindrical wall 76.

In various embodiments, the lower portion 84 of the base 72 further includes a lower collar 92 extending radially outwardly about a perimeter of a bottom end of the base 72.

A core 94 extends between and connects the upper collar 86 and lower collar 92 and has a transverse dimension (e.g., diameter) that is smaller than the transverse dimension (e.g. diameter) of the upper collar 86 and the lower collar 92. In various embodiments, the upper collar 86 and the lower collar 92 have a similar or substantially identical transverse dimension (e.g., diameter).

A plurality of openings 96 extend axially through a radially inner portion of the lower collar 92 into the core 94 and partially into the upper collar 86.

In various embodiments, the lower portion 84 of the base 72, and especially the upper collar 86, lower collar 92, and core 94 are configured as an interface for cooperation with a so-called puck conveyor or puck handling system. Exemplary conveyor systems include the X45 conveyor platform available from FlexLink AB, Göteborg, Sweden. In other embodiments, a base having a different shape and configuration may be used for other conveyor or handling mechanisms or for simply holding the article upright on a surface and not necessarily conveying the article, such as on a bench top or other surface.

An outer ring 66 may be rotatably disposed on the outer perimeter surface of the upper portion 74 of the base 72. Ring 66 includes an axially-extending cylindrical wall 68 and a rim flange 70 extending radially inwardly from a lower end of the cylindrical wall 68. Rim flange 70 is supported on raised inner peripheral surface 90 of the upper collar 86. In various embodiments, ring 66 is rotatably disposed on the base 72, and, in one embodiment, only an inner portion of the rim flange 70 is in contact with the raised surface 90 so as to minimize friction between the ring 66 and the base 72. Ring 66 is configured to engage side walls of a conveyor assembly, such as a puck conveyor, and is rotatable to minimize frictional rubbing between a side of the device 10 and the side walls of the conveyor assembly as the device is being conveyed. In various embodiments, ring 66 may be magnetic, or magnetically-responsive (e.g., a ferrous-based material) so as to magnetically engage a magnetic mechanism adjacent to a conveyor track to convey the device 10 along the track.

The midwall 100 include pin holes 102, 104, comprising through-holes formed axially through the midwall 100. In various embodiments, two pin holes, such as pin holes 102 and 104, are preferred, although alternate embodiments may include a single pin hole or more than two pin holes.

A recess 108 is formed in a center portion of the midwall 100 and comprises a first portion 112 and a second portion 114 having a radius that is smaller than the first portion 112. A raised peripheral shoulder 110 extends about a bottom perimeter of the recess 108, dividing the recess into the first portion 112 and second portion 114. A center through-hole 106 extends through the midwall 100 at a position that is generally coaxial with the recess 108.

The device 10 further includes a gripping element that is configured for circumferential expansion and contraction to grip and release, respectively, a tubular object placed into the device. In various embodiments, the gripping element comprises a torsion spring 44 generally comprising a plurality of coils 46 and having a lower end, or tail, 48 extending from a lower one of the coils 46 and an upper end, or tail, 50 extending from an upper one of the coils 46.

The actuator ring 52 having a generally annular configuration is disposed coaxially within the peripheral wall 76 of the upper portion 74 of the base 72. Actuator ring 52 includes a central hole 56 extending through a center portion of the ring 52. In various embodiments, central hole 56 is coaxially arranged with respect to the recess 108 formed in the midwall 100 of the base 72, and the diameter of the central hole 56 is generally equal to a diameter of the first portion of 112 of the recess 108.

The torsion spring 44 is disposed within the central hole 56 and extends down into the first portion 112 of the recess 108. The lower end 48 of the torsion spring 44 is fixed to the midwall 100 of the base 72 (e.g., into a slot). The upper end 50 of the torsion spring 44 is secured into a portion of the actuator ring 52 (e.g., into a slot). One or more engagement features 58 may be provided on a top surface of the actuator ring 52. In various embodiments, a radially inner end 60 of each of the engagement features 58 extends radially over an edge of the central hole 56 and thereby defines a spring retainer tip that extends over the torsion spring 42 disposed within the central hole 56 to retain the torsion spring 44 within the central hole 56. In various embodiments, the radially inner ends 60 of the engagement features 58 define an inner diameter sized to accommodate and support the intended object to be held within the device 10.

In various embodiments, a peripheral relief 54 is formed about a top peripheral edge of the actuator ring 52.

When installed within the peripheral wall 76 of the upper portion of 74 of base plate 72, the actuator ring 52 rests upon the midwall 100. In one embodiment, the actuator ring 52 is secured within the cylinder wall 76 by means of an inner retaining ring 118 disposed within the inner retaining ring groove 78 and extending partially into the peripheral relief 54. In various embodiments, the inner retaining ring 118 is formed of a fluoropolymer (e.g., Teflon®) or other compatible material. The actuator ring 52 is configured and installed so as to be rotatable with respect to the base 72. The rotation of the actuator ring 52 is facilitated by the engagement features 58, which may be engaged by the user's fingers, a special tool adapted to enable a user to apply a torque to the ring 52 while holding the base 72 stationary, or an automated or semi-automated machine constructed and arranged to effect rotation of the ring 52 with respect to the base 72 by means of prongs or other extensions that engage one or more of the openings 96 to hold the base 72.

Because the lower end 48 of the torsion spring 44 is secured to base of 72 and the upper end 50 of the torsion spring 44 is secured to the actuator ring 52, rotation of the actuator ring 52 with respect to the base 72 causes a relative radial translation between the upper end 50 and lower end 48, thereby circumferentially expanding or contracting the coils 46 of the torsion spring 44. The spring is configured such that a relative rotation between the upper and lower ends 48, 50 that results in an expansion of coils 46 will be against the spring bias of the torsion spring 44, whereas the bias will cause rotation between the upper and lower ends 48, 50 and a contraction of the coils 46 if there is no means or force holding the coils 46 in an expanded configuration.

The device 10 includes a locking mechanism that is coupled to the actuator element (e.g., actuator ring 52) and is configured to lock the actuator element in a position holding the gripping element (e.g., torsion spring 44) in the expanded configuration for receiving the elongated object. In an embodiment, the locking mechanism includes the spring plate 32, which is disposed within the lower portion 84 of the base 72. Spring plate 32 is generally circular and includes a center release pin 34 and two lock pins 36, 38 extending axially with respect to the spring plate 32. In various embodiments, the lock pins 36, 38 are disposed at a common radial distance from the center of the spring plate 32, and are radially aligned with each other. As shown in FIG. 3, spring plate 32 further includes a center spring recess 40 comprising a blind hole formed in a bottom surface of the spring plate 32. An actuator spring 30, e.g., a wave spring, is disposed within the spring recess 40 of the spring plate 32.

The spring plate 32 and the spring 30 are retained within the lower portion 84 of the base 72 by a retainer plate 20. The lock pins 36, 38 extend into the pin holes 102, 104, respectively, formed in the midwall 100 of base 72, thereby preventing relative rotation between the spring plate 32 and the base 72. The release pin 34 extends into the center hole 106 formed through the midwall 100.

The retainer plate 20 may be secured within the lower portion 84 of the base 72 by means of a friction fit between the perimeter of the retainer plate 20 and the lower portion 84 of the base. An adhesive, weld, or other means may be employed to further secure the retainer plate 20 within the lower portion 84 of the base 72. In various embodiments, the retainer plate 20 comprises a flat bottom 22 and a axially-projecting peripheral rim 24. In various embodiments, a circular RFID element 28 may be disposed within the retainer plate 20.

The spring plate 32 and the retainer plate/RFID element combination, are biased apart from each other by the axial spring 30 disposed with the spring recess 40 and bearing against top surface of the RFID element 28. In alternate embodiments, the RFID element 28 may be omitted, and the spring 30 may bear directly against a portion of the retainer plate 20. In embodiments including the RFID element 28, the RFID element 28 (or other automatic identification element) may be encoded with an identifying code which may be associated with the tubular element carried in the device 10 so that the tubular element may be automatically identified in any automated process or instrument in which the device 10 is employed.

The spring 30 biases the spring plate 32 against a bottom surface of the midwall 100 of the base 72. The lock pins 36, 38 of the spring plate 32 are somewhat longer than the pin holes 102, 104 formed through the midwall 100, so that the lock pins 36, 38 extend partially through the pin holes 102, 104 and above a top surface of the midwall 100.

The actuator ring 52 further includes lock holes 62, 64 comprising blind holes formed in the lower surface of the ring 52. The lock holes 62, 64 are radially aligned and are located at a common radial distance with respect to a center of the actuator ring 52 and are also located at the same radial distance as the lock pins 36, 38. As the actuator ring 52 is rotated with respect to the base 72, when the lock holes 62, 64 are aligned with the lock pins 36, 38, respectively, the bias of the spring 30 will push the spring plate 32 upwardly, thereby forcing the ends of the lock pins 36, 38 into the lock holes 62, 64 and thus preventing further rotation of the actuator ring 52 with respect to the base 72.

The device 10 includes a lock release mechanism configured to be triggered (e.g., actuated, activated, operated, etc.) by an elongated object being inserted into the device 10 to release the locking mechanism (e.g., spring plate 32). In an embodiment, the actuator ring 52 may be released from the spring plate 32 by pushing down on the release pin 34 of the spring plate 32 (e.g., by inserting the elongated object) to thereby move the spring plate 32, against the bias of the spring 30, to close a gap 42 between the bottom surface of spring plate 32 and the top surface of the RFID element 28 (or a top surface of retainer plate 20 if RFID element is omitted) to thereby withdraw the ends of the lock pins 36, 38 of the spring plate 32 from the lock holes 62, 64 of the actuator ring 52.

Various components of the device, such as the base 72, actuator ring 52, spring plate 32, and retainer plate 20, may be made from a material of suitable strength and machinability, such as metal, such as aluminum or plastic (e.g., Delrin® acetal resin). Ring 66, as noted above, may be made from a magnetic or magnetically-responsive materials. Springs 44 and 30 are preferably made from suitable spring material, such as spring steel.

Figure 4:
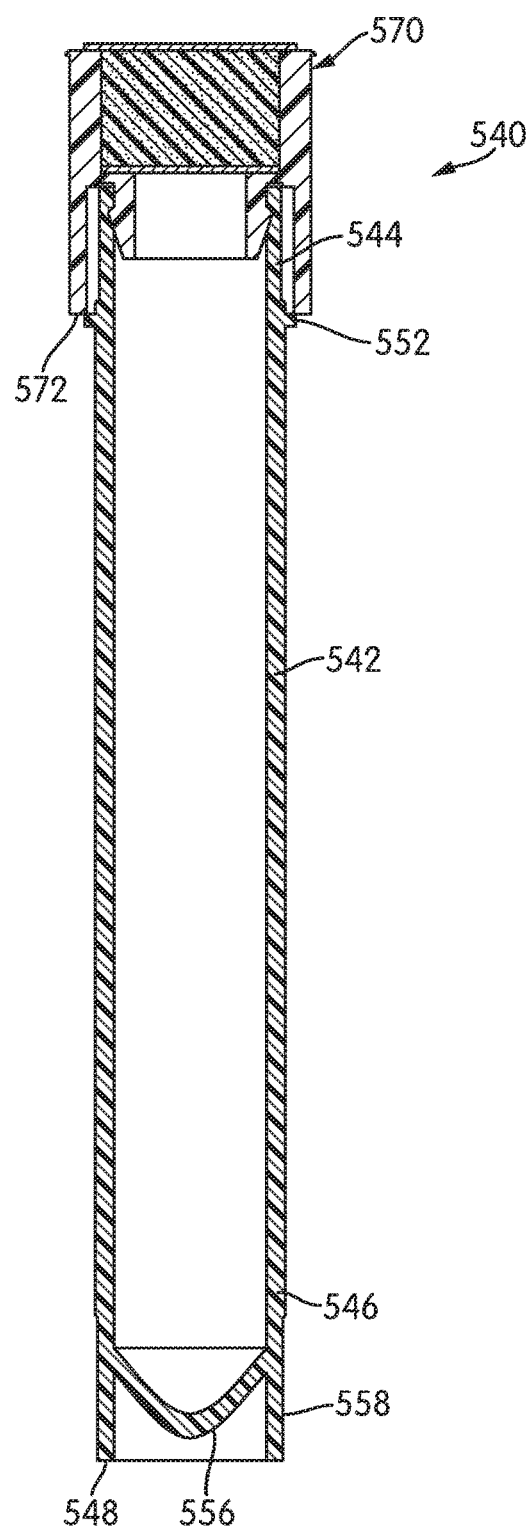
FIG. 4 is a side view in longitudinal cross-section of a receptacle that may be used in conjunction with the device.

An embodiment of a receptacle, such as cylindrical test tube, for use with the device 10 is generally indicated by reference number 540 in FIG. 4. FIG. 4 is a side cross-sectional view of the container 540. Container 540 is a generally tubular container having a sidewall 542 with a generally circular opening at an upper end 544 and a bottom wall 556 near the lower end 546 of the container. In the illustrated embodiment of FIG. 4, the bottom wall 556 has a conical shape.

The receptacle 540 can be made of any suitable material, and is preferably made from an injection molded plastic, such as polypropylene, or other similar material.

Receptacle 540 may be configured at its upper end 544 to cooperatively receive a cap 570 or other closure element for temporarily or permanently closing off the upper opening of the container 540. Features provided for cooperating with a closure element, such as cap 570, include external threads that cooperate with mating internal threads of the cap 570. As an alternative, threads may be formed on the interior surface of the sidewall 542 and configured to cooperate with mating threads formed on an exterior surface of the cap, or cooperating flanges, recesses, and/or tabs may be provided to allow the cap 570 to be snapped into place on the container 540.

A ring flange 552 may be included which extends circumferentially about the sidewall 542 of the container 540 and is abutted by a bottom edge 572 of the cap 570. Suitable caps for use with the container 540 include a penetrable cap described by Kacian et al. in U.S. Pat. No. 6,893,612.

In various embodiments of the container, an axially depending skirt 558 extends from the side wall 542 below the conical bottom wall 556 at the lower end 546 of the container 540. In the illustrated embodiment, the depending skirt 558 comprises an axial extension of the sidewall 542 below the conical bottom wall 546. A lower end of the skirt 558 defines an annular edge ring 548 that is generally perpendicular to a longitudinal axis of the container 540.

To place an elongated object, such as container 540, into the device 10, the device may first be put into the open position. The actuator ring 52 is rotated, such as by hand or with a tool or machine engaging the engagement features 58, with respect to the base plate 72 against the bias of the torsion spring 44 to expand the torsion spring. The actuator ring 52 is rotated until the lock pins 36, 38 of the spring plate 32 align with the lock holes 62, 64, respectively, of the actuator ring 52. At that point, the spring 30 forces the lock pins 36, 38 into the lock holes 62, 64, thereby locking the actuator ring against further rotation with respect to the base 72 and locking the torsion spring 44 in the expanded position.

In the expanded position, the coils 46 of the torsion spring 44 have an inside diameter that is wider than the diameter of the portion of the container that is to be inserted into the torsion spring 44. An end of the container 540, e.g., the bottom end, is inserted into the central hole 56 within the actuator ring 52 and inside the coils 46 of the spring 44. The container 540 is inserted until a bottom end thereof (e.g., the bottom of conical bottom wall 546) contacts the center release pin 34. Further pushing of the container 540 against the release pin 34 overcomes the bias of the spring 30 and moves the spring plate 32, and withdraws the lock pins 36, 38 from the lock holes 62, 64. With the lock pins 36, 38 withdrawn from the lock holes 62, 64, the actuator plate 52 and the base 72 are no longer rotationally coupled to one another, and the coils 46 of the torsion spring 44 are able to contract around the end of the container 540 to thereby hold the container within the central hole 56.

In some embodiments, it may be possible leave the device in a closed position when inserting an elongated object into the device 10 and to force the object into the torsion spring 44, whereby forcing the object—which may include twisting the object—causes enough circumferential expansion of the coils 46 to enable the object to be inserted.

With the end of the container held within the device 10, the device 10 can be placed on a conveyor or other handling mechanism or supporting surface configured to support and/or convey the device 10 to thereby support and/or convey the container in an upright orientation. In various embodiments, because the container is held in the device 10 at one end thereof (e.g., the lower end), and because of the relatively low profile of the device 10 relative to the length of container, a label(s) or other indicia, such as a bar code, on the side of the container will not be covered or otherwise obstructed by the device 10.

Figure 5:
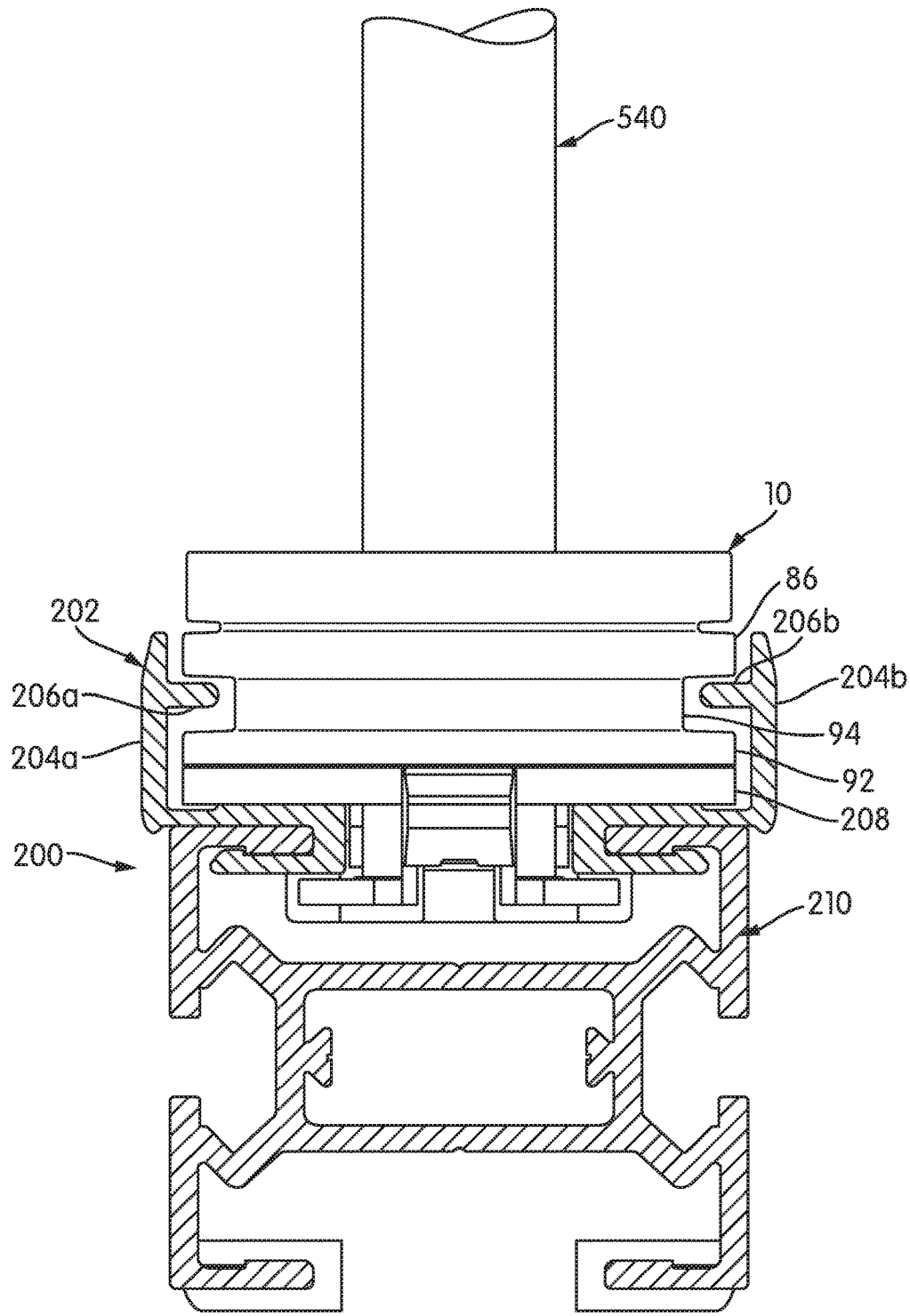
FIG. 5 a view of the device carried on an exemplary conveyor platform, where the conveyor platform is shown in cross-section.

FIG. 5 shows the device 10, with a container 540 inserted therein, carried on an exemplary conveyor platform 200. Conveyor platform 200 may be, for example, an X45 conveyor platform available from FlexLink AB, Göteborg, Sweden. The exemplary conveyor platform 200 includes a track 202 supported on a frame 210. Track 202 includes opposed sidewalls 204a, 204b, each having a respective retainer flange 206a, 206b extending laterally for at least a portion of the length of the track 202. Device 10 is supported on a surface 208, which may comprise a moving belt or other moving surface for conveying objects supported thereon. The retainer flanges 206a, 206b of the side walls 204a, 204b extend toward the core 94 of the device 10, between the upper collar 86 and the lower collar 92, to thereby hold the device 10 onto the track 202.

EXEMPLARY EMBODIMENTS

Embodiment 1

A device for releasably securing an elongated object in a predetermined orientation with respect to the device, the device comprising: a gripping element configured for circumferential expansion and contraction; an actuator element coupled to the gripping element and configured to effect circumferential expansion of the gripping element, upon operation of the actuator element, to an expanded configuration able to receive an end of the elongated object; a locking mechanism coupled to the actuator element and configured to lock the actuator element in a position holding the gripping element in the expanded configuration; and a lock release mechanism configured to be triggered by an elongated object inserted into the device to release the locking mechanism, wherein the gripping element is circumferentially biased so as to cause the gripping element to circumferentially contract around the received end of the elongated object upon release of the locking mechanism.

Embodiment 2

The device of embodiment 1, further comprising a base and wherein the actuator element comprises an actuator ring rotatably mounted within a portion of the base such that partial rotation of the actuator ring with respect to the base in a first direction causes circumferential expansion of the gripping element and circumferential contraction of the gripping element causes partial rotation of the actuator ring with respect to the base in a second direction opposite the first direction.

Embodiment 3

The device of embodiment 2, wherein the gripping element comprises a torsion spring having coils defining a circumference of the gripping element, a first end fixed to the base, and a second end fixed to the actuator ring, wherein the coils are configured to circumferentially expand against a bias of the torsion spring when the actuator ring is rotated in the first direction with respect to the base to move the second end angularly in the first direction with respect to the first end, and the coils are configured to contract when the bias of the torsion spring moves the second end and the actuator ring angularly in the second direction with respect to the first end and the base.

Embodiment 4

The device of embodiment 3, wherein the torsion spring is at least partially disposed with an opening formed at the center of the actuator ring.

Embodiment 5

The device of any one of embodiments 1 to 4, wherein the locking mechanism comprises: a spring plate with at least two lock pins protruding therefrom; a spring constructed and arranged to bias the spring plate toward the actuator element; and pin recesses formed in a side of the actuator element facing the spring plate, and corresponding in number with the number of lock pins protruding from the spring plate, wherein the lock pins are moved into alignment with the pin recesses when operation of the actuator element causes circumferential expansion of the gripping element to the expanded configuration so that the spring thereby moves the spring plate toward the actuator element and pushes the lock pins into the pin recesses to rotationally lock the actuator element with respect to the spring plate.

Embodiment 6

The device of embodiment 5, wherein the release mechanism comprises a release pin protruding from the spring plate and constructed and arranged to be contacted by an elongated object inserted into the device and so as to push the spring plate against the bias of the spring away from the actuator element until the lock pins of the spring plate are withdrawn from the pin recesses of the actuator element.

Embodiment 7

The device of any one of embodiments 1 to 6, further comprising a circular base having an upper portion and a lower portion, wherein the lower portion includes an upper radial flange and a lower radial flange and a core disposed between the upper and lower radial flanges, wherein the core has a smaller diameter than either of the upper and lower radial flanges.

Embodiment 8

The device of any one of embodiments 1 to 7, wherein the base is configured to cooperate with a conveyor mechanism to transport the device and a container held thereby along the conveyor mechanism.

Embodiment 9

The device of any one of embodiments 1 to 8, wherein the base is circular and wherein the device further includes an outer ring disposed on the base so as to be rotatable with respect to the base about a central axis of the circular base.

Embodiment 10

The device of 9, wherein the outer ring is made from a magnetic or magnetically-responsive material.

Embodiment 11

The device of any one of embodiments 1-10, further comprising an automatic identification element encoded with an identifying code so that the device or an object carried thereby can be automatically identified in an automated process or instrument in which the device is employed.

Embodiment 12

The device of embodiment 11, wherein the automatic identification element comprises an RFID tag.

Embodiment 13

A system for transporting an elongated object disposed in predetermined orientation, the system comprising: a) a holding device for releasably securing an elongated object in a predetermined orientation with respect to the device, the holding device comprising: 1) a gripping element configured for circumferential expansion and contraction; 2) an actuator element coupled to the gripping element and configured to effect circumferential expansion of the gripping element, upon operation of the actuator element, to an expanded configuration able to receive an end of the elongated object; 3) a locking mechanism coupled to the actuator element and configured to lock the actuator element in a position holding the gripping element in the expanded configuration; and 4) a lock release mechanism configured to be triggered by an elongated object inserted into the device to release the locking mechanism, wherein the gripping element is circumferentially biased so as to cause the gripping element to circumferentially contract around the received end of the elongated object upon release of the locking mechanism; and b) a conveyor platform configured to support and convey the holding device.

Embodiment 14

The system of embodiment 13, wherein the holding device comprises a base having a lower collar extending laterally therefrom, and the conveyor platform comprises a track having a side wall with a retainer flange extending laterally therefrom, wherein the retainer flange extends over the lower collar when the holding device is supported on the conveyor platform.

Embodiment 15

The system of embodiment 14, wherein the base of the holding device has an upper collar extending laterally therefrom at a spaced apart position above the lower collar, and wherein the retainer flange extends laterally between the lower collar and the upper collar when the holding device is supported on the conveyor platform.

Embodiment 16

The system of any one of embodiments 13 to 15, wherein the conveyor platform includes a movable belt on which the holding device is supported and which is configured to convey the holding device.

Embodiment 17

The system of any one of embodiments 14 to 16, wherein the actuator element of the holding device comprises an actuator ring rotatably mounted within a portion of the base such that partial rotation of the actuator ring with respect to the base in a first direction causes circumferential expansion of the gripping element and circumferential contraction of the gripping element causes partial rotation of the actuator ring with respect to the base in a second direction opposite the first direction.

Embodiment 18

The system of embodiment 17, wherein the gripping element of the holding device comprises a torsion spring having coils defining a circumference of the gripping element, a first end fixed to the base, and a second end fixed to the actuator ring, wherein the coils are configured to circumferentially expand against a bias of the torsion spring when the actuator ring is rotated in the first direction with respect to the base to move the second end angularly in the first direction with respect to the first end, and the coils are configured to contract when the bias of the torsion spring moves the second end and the actuator ring angularly in the second direction with respect to the first end and the base.

Embodiment 19

The system of embodiment 18, wherein the torsion spring is at least partially disposed with an opening formed at the center of the actuator ring.

Embodiment 20

The system of any one of embodiments 13 to 19, wherein the locking mechanism of the holding device comprises: a spring plate with at least two lock pins protruding therefrom; a spring constructed and arranged to bias the spring plate toward the actuator element; and pin recesses formed in a side of the actuator element facing the spring plate, and corresponding in number with the number of lock pins protruding from the spring plate, wherein the lock pins are moved into alignment with the pin recesses when operation of the actuator element causes circumferential expansion of the gripping element to the expanded configuration so that the spring thereby moves the spring plate toward the actuator element and pushes the lock pins into the pin recesses to rotationally lock the actuator element with respect to the spring plate.

Embodiment 21

The system of embodiment 20, wherein the release mechanism of the holding device comprises a release pin protruding from the spring plate and constructed and arranged to be contacted by an elongated object inserted into the device and so as to push the spring plate against the bias of the spring away from the actuator element until the lock pins of the spring plate are withdrawn from the pin recesses of the actuator element.

Embodiment 22

The system of any one of embodiments 14 to 21, wherein the base of the holding device is circular and wherein the device further includes an outer ring disposed on the base so as to be rotatable with respect to the base about a central axis of the circular base.

Embodiment 23

The system of 22, wherein the outer ring is made from a magnetic or magnetically-responsive material.

Embodiment 24

The system of any one of embodiments 13-23, wherein the holding device further comprises an automatic identification element encoded with an identifying code so that the holding device or an object carried thereby can be automatically identified in an automated process or instrument in which the device is employed.

Embodiment 25

The system of embodiment 24, wherein the automatic identification element of the holding device comprises an RFID tag.

While the subject matter of this disclosure has been described and shown in considerable detail with reference to certain illustrative embodiments, including various combinations and sub-combinations of features, those skilled in the art will readily appreciate other embodiments and variations and modifications thereof. Moreover, the descriptions of such embodiments, combinations, and sub-combinations is not intended to convey that features or combinations of features, other than those expressly recited in the claims, are required. Accordingly, the scope of this disclosure is intended to include all modifications and variations encompassed within the scope of the following appended claims.

The invention claimed is:

1. A device for releasably securing an elongated object in a predetermined orientation with respect to the device, the device comprising:
   a gripping element configured for circumferential expansion and contraction;
   an actuator element coupled to the gripping element and configured to effect circumferential expansion of the gripping element, upon operation of the actuator element, to an expanded configuration able to receive an end of the elongated object;
   a locking mechanism coupled to the actuator element and configured to lock the actuator element in a position holding the gripping element in the expanded configuration; and
   a lock release mechanism configured to be triggered by an elongated object inserted into the device to release the locking mechanism, wherein the gripping element is circumferentially biased so as to cause the gripping element to circumferentially contract around the received end of the elongated object upon release of the locking mechanism.

2. The device of claim 1, further comprising a base and wherein the actuator element comprises an actuator ring rotatably mounted within a portion of the base such that partial rotation of the actuator ring with respect to the base in a first direction causes circumferential expansion of the gripping element and circumferential contraction of the gripping element causes partial rotation of the actuator ring with respect to the base in a second direction opposite the first direction.

3. The device of claim 2, wherein the gripping element comprises a torsion spring having coils defining a circumference of the gripping element, a first end fixed to the base, and a second end fixed to the actuator ring, wherein the coils are configured to circumferentially expand against a bias of the torsion spring when the actuator ring is rotated in the first direction with respect to the base to move the second end angularly in the first direction with respect to the first end, and the coils are configured to contract when the bias of the torsion spring moves the second end and the actuator ring angularly in the second direction with respect to the first end and the base.

4. The device of claim 3, wherein the torsion spring is at least partially disposed with an opening formed at the center of the actuator ring.

5. The device of claim 1, wherein the locking mechanism comprises a spring plate with at least two lock pins protruding therefrom and a spring constructed and arranged to bias the spring plate toward the actuator element; and
   wherein the actuator element comprises pin recesses formed in a side of the actuator element facing the spring plate, and corresponding in number with the number of lock pins protruding from the spring plate, wherein the lock pins are moved into alignment with the pin recesses when operation of the actuator element causes circumferential expansion of the gripping element to the expanded configuration and the spring moves the spring plate toward the actuator element and pushes the lock pins into the pin recesses to rotationally lock the actuator element with respect to the spring plate.

6. The device of claim 5, wherein the lock release mechanism comprises a release pin protruding from the spring plate and constructed and arranged to be contacted by an elongated object inserted into the device and so as to push the spring plate against the bias of the spring away from the actuator element until the lock pins of the spring plate are withdrawn from the pin recesses of the actuator element.

7. The device of claim 1, further comprising a circular base having an upper portion and a lower portion, wherein the lower portion includes an upper radial flange and a lower radial flange and a core disposed between the upper and lower radial flanges, wherein the core has a smaller diameter than either of the upper and lower radial flanges.

8. The device of claim 7, wherein the base is configured to cooperate with a conveyor mechanism to transport the device and a container held thereby along the conveyor mechanism.

9. The device of claim 7, wherein the device further includes an outer ring disposed on the base so as to be rotatable with respect to the base about a central axis of the circular base.

10. The device of 9, wherein the outer ring is made from a magnetic or magnetically-responsive material.

11. The device of claim 1, further comprising an automatic identification element encoded with an identifying code so that the device or an object carried thereby can be automatically identified in an automated process or instrument in which the device is employed.

12. The device of claim 11, wherein the automatic identification element comprises an RFID tag.

13. A system for transporting an elongated object disposed in a predetermined orientation, the system comprising:
   a) a holding device for releasably securing an elongated object in a predetermined orientation with respect to the holding device, the holding device comprising:
      1) a gripping element configured for circumferential expansion and contraction;
      2) an actuator element coupled to the gripping element and configured to effect circumferential expansion of the gripping element, upon operation of the actuator element, to an expanded configuration able to receive an end of the elongated object;
      3) a locking mechanism coupled to the actuator element and configured to lock the actuator element in a position holding the gripping element in the expanded configuration; and
      4) a lock release mechanism configured to be triggered by an elongated object inserted into the holding device to release the locking mechanism, wherein the gripping element is circumferentially biased so as to cause the gripping element to circumferentially contract around the received end of the elongated object upon release of the locking mechanism; and
   b) a conveyor platform configured to support and convey the holding device.

14. The system of claim 13, wherein the holding device comprises a base having a lower collar extending laterally therefrom, and the conveyor platform comprises a track having a side wall with a retainer flange extending laterally therefrom, wherein the retainer flange extends over the lower collar when the holding device is supported on the conveyor platform.

15. The system of claim 14, wherein the base of the holding device has an upper collar extending laterally therefrom at a spaced apart position above the lower collar, and wherein the retainer flange extends laterally between the lower collar and the upper collar when the holding device is supported on the conveyor platform.

16. The system claim 14, wherein the actuator element of the holding device comprises an actuator ring rotatably mounted within a portion of the base such that partial rotation of the actuator ring with respect to the base in a first direction causes circumferential expansion of the gripping element and circumferential contraction of the gripping element causes partial rotation of the actuator ring with respect to the base in a second direction opposite the first direction.

17. The system of claim 16, wherein the gripping element of the holding device comprises a torsion spring having coils defining a circumference of the gripping element, a first end fixed to the base, and a second end fixed to the actuator ring, wherein the coils are configured to circumferentially expand against a bias of the torsion spring when the actuator ring is rotated in the first direction with respect to the base to move the second end angularly in the first direction with respect to the first end, and the coils are configured to contract when the bias of the torsion spring moves the second end and the actuator ring angularly in the second direction with respect to the first end and the base.

18. The system of claim 17, wherein the torsion spring is at least partially disposed with an opening formed at the center of the actuator ring.

19. The system of claim 14, wherein the base of the holding device is circular and wherein the holding device further includes an outer ring disposed on the base so as to be rotatable with respect to the base about a central axis of the circular base.

20. The system of 19, wherein the outer ring is made from a magnetic or magnetically-responsive material.

21. The system of claim 13, wherein the conveyor platform includes a movable belt on which the holding device is supported and which is configured to convey the holding device.

22. The system of claim 13, wherein the locking mechanism of the holding device comprises a spring plate with at least two lock pins protruding therefrom and a spring constructed and arranged to bias the spring plate toward the actuator element; and
   wherein the actuator element comprises pin recesses formed in a side of the actuator element facing the spring plate, and corresponding in number with the number of lock pins protruding from the spring plate, wherein the lock pins are moved into alignment with the pin recesses when operation of the actuator element causes circumferential expansion of the gripping element to the expanded configuration and the spring moves the spring plate toward the actuator element and pushes the lock pins into the pin recesses to rotationally lock the actuator element with respect to the spring plate.

23. The system of claim 22, wherein the release mechanism of the holding device comprises a release pin protruding from the spring plate and constructed and arranged to be contacted by an elongated object inserted into the holding device and so as to push the spring plate against the bias of the spring away from the actuator element until the lock pins of the spring plate are withdrawn from the pin recesses of the actuator element.

24. The system of claim 13, wherein the holding device further comprises an automatic identification element encoded with an identifying code so that the holding device or an object carried thereby can be automatically identified in an automated process or instrument in which the holding device is employed.

25. The system of claim 24, wherein the automatic identification element of the holding device comprises an RFID tag.

* * * * *